US011304600B2

(12) United States Patent
Kuramoto

(10) Patent No.: US 11,304,600 B2
(45) Date of Patent: Apr. 19, 2022

(54) LIGHT SOURCE DEVICE, ENDOSCOPE SYSTEM, AND METHOD OF OPERATING LIGHT SOURCE DEVICE

(71) Applicant: FUJIFILM Corporation, Tokyo (JP)

(72) Inventor: Masayuki Kuramoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 80 days.

(21) Appl. No.: 16/787,509

(22) Filed: Feb. 11, 2020

(65) Prior Publication Data

US 2020/0170493 A1 Jun. 4, 2020

Related U.S. Application Data

(63) Continuation of application No. PCT/JP2018/030290, filed on Aug. 14, 2018.

(30) Foreign Application Priority Data

Aug. 22, 2017 (JP) ................................. 2017-159549

(51) Int. Cl.
*A61B 1/00* (2006.01)
*A61B 1/06* (2006.01)
(Continued)

(52) U.S. Cl.
CPC ........ *A61B 1/0676* (2013.01); *A61B 1/00006* (2013.01); *A61B 1/045* (2013.01);
(Continued)

(58) Field of Classification Search
CPC ... A61B 1/0676; A61B 1/00006; A61B 1/045; A61B 1/0638; A61B 1/0684;
(Continued)

(56) References Cited

U.S. PATENT DOCUMENTS

2014/0031623 A1 1/2014 Kagaya
2014/0364690 A1* 12/2014 Seto ..................... A61B 1/0005
600/109
(Continued)

FOREIGN PATENT DOCUMENTS

JP 2012-050641 A 3/2012
JP 2014-014022 A 1/2014
(Continued)

OTHER PUBLICATIONS

International Search Report issued in PCT/JP2018/030290; dated Oct. 30, 2018.
(Continued)

*Primary Examiner* — Timothy J Neal
*Assistant Examiner* — Sung Ham
(74) *Attorney, Agent, or Firm* — Studebaker & Brackett PC

(57) ABSTRACT

A light source unit emits light in a plurality of wavelength ranges. The light source unit can change the light emission ratio of light in each wavelength range. In a case where the switching of first illumination light having a first light emission ratio and second illumination light having a second light emission ratio different from the first light emission ratio is performed, switching-period-illumination light having a switching-period-light-emission ratio different from the first light emission ratio and the second light emission ratio is emitted in a switching period of at least one or more frames.

11 Claims, 12 Drawing Sheets

(51) Int. Cl.
*A61B 1/045* (2006.01)
*A61B 1/005* (2006.01)
(52) U.S. Cl.
CPC .......... *A61B 1/0638* (2013.01); *A61B 1/0684* (2013.01); *A61B 1/0051* (2013.01); *A61B 1/00096* (2013.01)
(58) Field of Classification Search
CPC . A61B 1/00096; A61B 1/0051; A61B 1/0653; A61B 1/0661; A61B 1/05; A61B 1/0005; A61B 1/3137; A61B 1/00186; A61B 1/00009; A61B 1/0017; A61B 1/07; G02B 23/24; G02B 23/26; G06T 2207/10068; G06T 7/0012
See application file for complete search history.

(56) References Cited

U.S. PATENT DOCUMENTS

| | | | | |
|---|---|---|---|---|
| 2015/0138328 | A1* | 5/2015 | Yokohama | H04N 5/372 348/65 |
| 2015/0245002 | A1* | 8/2015 | Kuramoto | A61B 1/00009 348/70 |
| 2015/0272429 | A1* | 10/2015 | Shigeta | H04N 9/04521 348/65 |
| 2016/0120398 | A1* | 5/2016 | Kubo | H04N 5/3456 348/68 |
| 2017/0006202 | A1 | 1/2017 | Otani et al. | |
| 2017/0020378 | A1* | 1/2017 | Godo | H04N 5/2256 |
| 2017/0086648 | A1 | 3/2017 | Kamee et al. | |

FOREIGN PATENT DOCUMENTS

| | | |
|---|---|---|
| JP | 2014-023626 A | 2/2014 |
| JP | 2016-209517 A | 12/2016 |
| JP | 3042798 B2 | 12/2016 |
| JP | 2017-000193 A | 1/2017 |
| JP | 2017-012395 A | 1/2017 |
| WO | 2015/190255 A1 | 12/2015 |

OTHER PUBLICATIONS

International Preliminary Report on Patentability and Written Opinion issued in PCT/JP2018/030290; daed Feb. 25, 2020.

* cited by examiner

LIGHT SOURCE DEVICE, ENDOSCOPE SYSTEM, AND METHOD OF OPERATING LIGHT SOURCE DEVICE

CROSS-REFERENCE TO RELATED APPLICATIONS

This application is a Continuation of PCT International Application No. PCT/JP2018/030290 filed on 14 Aug. 2018, which claims priority under 35 U.S.C § 119(a) to Japanese Patent Application No. 2017-159549 filed on 22 Aug. 2017. The above application is hereby expressly incorporated by reference, in its entirety, into the present application.

BACKGROUND OF THE INVENTION

1. Field of the Invention

The present invention relates to a light source device, an endoscope system, and a method of operating the light source device that switch and emit plural kinds of illumination light.

2. Description of the Related Art

In recent years, an endoscope system comprising a light source device, an endoscope, and a processor device has been widely used in a medical field. In the endoscope system, an object to be observed is irradiated with illumination light from an endoscope, and the image of the object to be observed is displayed on a monitor on the basis of RGB image signals that are obtained in a case where the image of the object to be observed, which is being illuminated with the illumination light, is picked by an image pickup element of the endoscope.

Further, a plurality of observation modes are provided in the endoscope system so that illumination light used to irradiate an object to be observed can be switched and image processing for the image of the object to be observed can be switched in accordance with the purpose of diagnosis. There is a case where problems associated with the switching of a mode are generated at the time of the switching of an observation mode.

For example, as disclosed in JP2012-50641A, predetermined time (rise time) is required until light having a target intensity can be emitted from a light source to be used after switching (rise time) in a case where a light source in use is switched by the switching of a mode. Since the tone of an image obtained for the rise time is not stable, a timing when image processing is switched by the switching of a mode is adapted to be controlled in JP2012-50641A.

Further, as disclosed in JP6042798B, there is a case where processing is not be performed using a parameter corresponding to a switched mode in a case where the timing of the switching of illumination light and the timing of the acquisition of an image do not coincide with each other at the time of the switching of a mode. In contrast, in JP6042798B, the mode of an acquired image is determined from the acquired image and processing is adapted to be performed using a parameter corresponding to the mode obtained from the result of the determination.

SUMMARY OF THE INVENTION

In some endoscope systems, there is a case where time required for the switching of image processing is longer than time required for the switching of a light source in a case where an operation for switching a mode is performed. In this case, an abnormal image, which has been subjected to image processing not corresponding to a light source to be used after the switching of a mode, may be displayed at the time of the switching of a mode. For example, in a case where light is switched to white light from special light including many short-wavelength components, such as blue light, by the switching of a mode, image processing corresponding to the special light may be performed on an image of white light. In this case, a reddish image is displayed. Accordingly, there is a request for the suppression of the generation of an abnormal image associated with the switching of a mode at the time of the switching of a mode.

An object of the invention is to provide a light source device, an endoscope system, and a method of operating the light source device that can suppress the generation of an abnormal image associated with the switching of a mode at the time of the switching of a mode.

A light source device according to an aspect of the invention comprises a light source unit and a light source control unit. The light source unit emits light in a plurality of wavelength ranges and is capable of changing a light emission ratio of light in each wavelength range. In a switching period of at least one or more frames in a case where the light source control unit performs switching of first illumination light having a first light emission ratio and second illumination light having a second light emission ratio different from the first light emission ratio, the light source control unit performs control to emit switching-period-illumination light having a switching-period-light-emission ratio different from the first light emission ratio and the second light emission ratio.

It is preferable that the light source control unit performs first switching-period-light-emission control, which emits the switching-period-illumination light while changing the switching-period-light-emission ratio, in the switching period. It is preferable that control, which makes the switching-period-light-emission ratio become closer to a light emission ratio of illumination light to be emitted after the switching as it goes to a later frame in the switching period, is performed in the first switching-period-light-emission control. It is preferable that the light source control unit performs second switching-period-light-emission control, which emits the switching-period-illumination light of which the switching-period-light-emission ratio is between the first light emission ratio and the second light emission ratio, in the switching period.

It is preferable that, in a case where the light source control unit performs any one of first switching-period-light-emission control, which emits the switching-period-illumination light while changing the switching-period-light-emission ratio, in the switching period or second switching-period-light-emission control, which emits the switching-period-illumination light of which the switching-period-light-emission ratio is between the first light emission ratio and the second light emission ratio, in the switching period, the switching period in a case where the first switching-period-light-emission control is performed is set to be longer than the switching period in a case where the second switching-period-light-emission control is performed.

An endoscope system according to another aspect of the invention comprises: a light source device including a light source unit and a light source control unit; and a processor device. The light source unit emits light in a plurality of wavelength ranges and is capable of changing a light emission ratio of light in each wavelength range. In a case where the light source control unit performs switching of first illumination light having a first light emission ratio and second illumination light having a second light emission ratio different from the first light emission ratio, the light source control unit performs control to emit switching-period-illumination light having a switching-period-light-emission ratio different from the first light emission ratio and the second light emission ratio in a switching period of at least one or more frames. The processor device performs processing for first illumination light on a first image obtained from image pickup of an object to be observed illuminated with the first illumination light and performs processing for second illumination light on a second image obtained from image pickup of an object to be observed illuminated with the second illumination light. The light source control unit performs control to make the switching-period-light-emission ratio correspond to specific color balance at a timing when processing has been switched to the processing for second illumination light from the processing for first illumination light.

It is preferable that the processing for first illumination light is gain processing for first illumination light or color adjustment processing for first illumination light and the processing for second illumination light is gain processing for second illumination light or color adjustment processing for second illumination light.

A method of operating a light source device including a light source unit according to another aspect of the invention comprises an illumination light switching step. The light source unit emits light in a plurality of wavelength ranges and is capable of changing a light emission ratio of light in each wavelength range. In the illumination light switching step, a light source control unit performs control to emit switching-period-illumination light having a switching-period-light-emission ratio different from a first light emission ratio and a second light emission ratio in a switching period of at least one or more frames in a case where switching of first illumination light having the first light emission ratio and second illumination light having the second light emission ratio different from the first light emission ratio is performed.

It is preferable that, in the illumination light switching step, the light source control unit performs first switching-period-light-emission control, which emits the switching-period-illumination light while changing the switching-period-light-emission ratio, in the switching period. It is preferable that, in the illumination light switching step, the light source control unit performs second switching-period-light-emission control, which emits the switching-period-illumination light of which the switching-period-light-emission ratio is between the first light emission ratio and the second light emission ratio, in the switching period.

According to the invention, it is possible to suppress the generation of an abnormal image associated with the switching of a mode at the time of the switching of a mode.

DESCRIPTION OF THE PREFERRED EMBODIMENTS

First Embodiment

Figure 1:
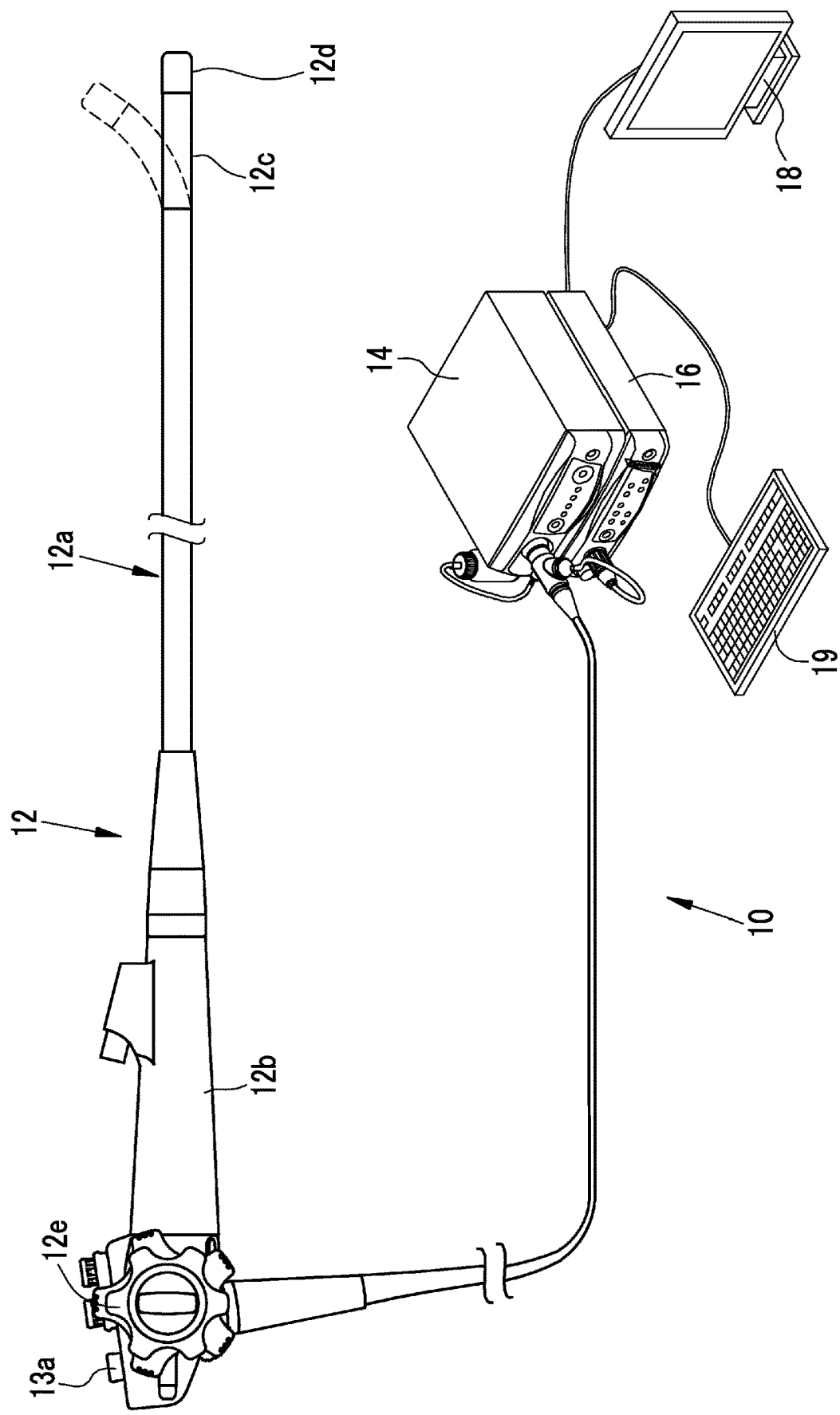
FIG. 1 is a diagram showing the appearance of an endoscope system according to a first embodiment.

As shown in FIG. 1, an endoscope system 10 according to a first embodiment includes an endoscope 12, a light source device 14, a processor device 16, a monitor 18, and a console 19. The endoscope 12 is optically connected to the light source device 14, and is electrically connected to the processor device 16. The endoscope 12 includes an insertion part 12a that is to be inserted into an object to be examined, an operation part 12b that is provided at the proximal end portion of the insertion part 12a, and a bendable part 12c and a distal end part 12d that are provided on the distal end side of the insertion part 12a. In a case where angle knobs 12e of the operation part 12b are operated, the bendable part 12c is operated to be bent. As the bendable part 12c is operated to be bent, the distal end part 12d faces in a desired direction. The console 19 includes a mouse and the like in addition to a keyboard shown in FIG. 1.

Further, the operation part 12b is provided with a mode changeover SW 13a in addition to the angle knobs 12e. The mode changeover SW 13a is used for an operation for switching a normal observation mode, a first special observation mode, a second special observation mode, and a multi-observation mode. The normal observation mode is a mode where a normal image is displayed on the monitor 18. The first special observation mode is a mode where a first special image in which superficial blood vessels are emphasized is displayed on the monitor 18. The second special observation mode is a mode where a second special image in which deep blood vessels are emphasized is displayed on the monitor 18.

A foot switch may be used as a mode switching unit, which is used to switch a mode, other than the mode changeover SW 13a. A multi-observation mode where a mode is automatically switched may be provided instead of manually switching a mode by the operation of the mode changeover SW 13a. For example, the first special observation mode and the second special observation mode are automatically switched in the multi-observation mode. Further, the operation part 12b is provided with a freeze button (not shown) that is used to acquire a static image. In a case where a user detects a portion that seems to be effective for diagnosis, the mode changeover SW 13a and the freeze button may be operated alternately.

The processor device 16 is electrically connected to the monitor 18 and the console 19. The monitor 18 outputs and displays image information and the like. The console 19 functions as a user interface (UI) that receives an input operation, such as function settings. An external recording unit (not shown), which records image information and the like, may be connected to the processor device 16.

Figure 2:
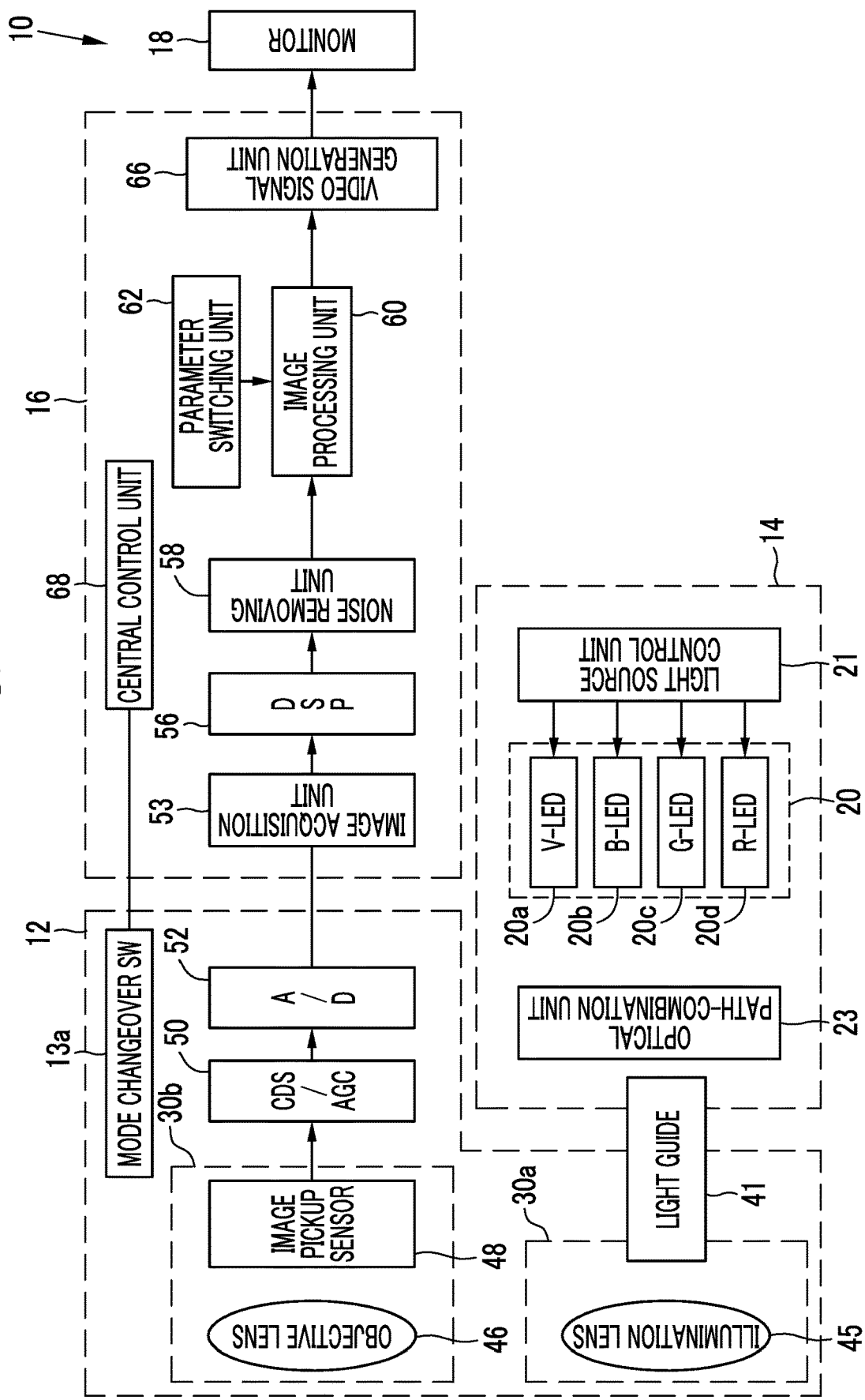
FIG. 2 is a block diagram showing the functions of the endoscope system according to the first embodiment.

As shown in FIG. 2, the light source device 14 includes a light source unit 20, a light source control unit 21, and an optical path-combination unit 23. The light source unit 20 can emit light in a plurality of wavelength ranges, and can change the light emission ratio of light in each wavelength range. The light source unit 20 includes a violet light emitting diode (V-LED) 20a, a blue light emitting diode (B-LED) 20b, a green light emitting diode (G-LED) 20c, and a red light emitting diode (R-LED) 20d to emit light in a plurality of wavelength ranges. A laser diode (LD) may be used instead of the LED.

The light source control unit 21 controls the drive of the LEDs 20a to 20d. The optical path-combination unit 23 combines the optical paths of pieces of light that are emitted from the four color LEDs 20a to 20d and have four colors. The inside of an object to be examined is irradiated with the pieces of light, which are combined by the optical path-combination unit 23, through a light guide 41 inserted into the insertion part 12a and an illumination lens 45.

Figure 3:
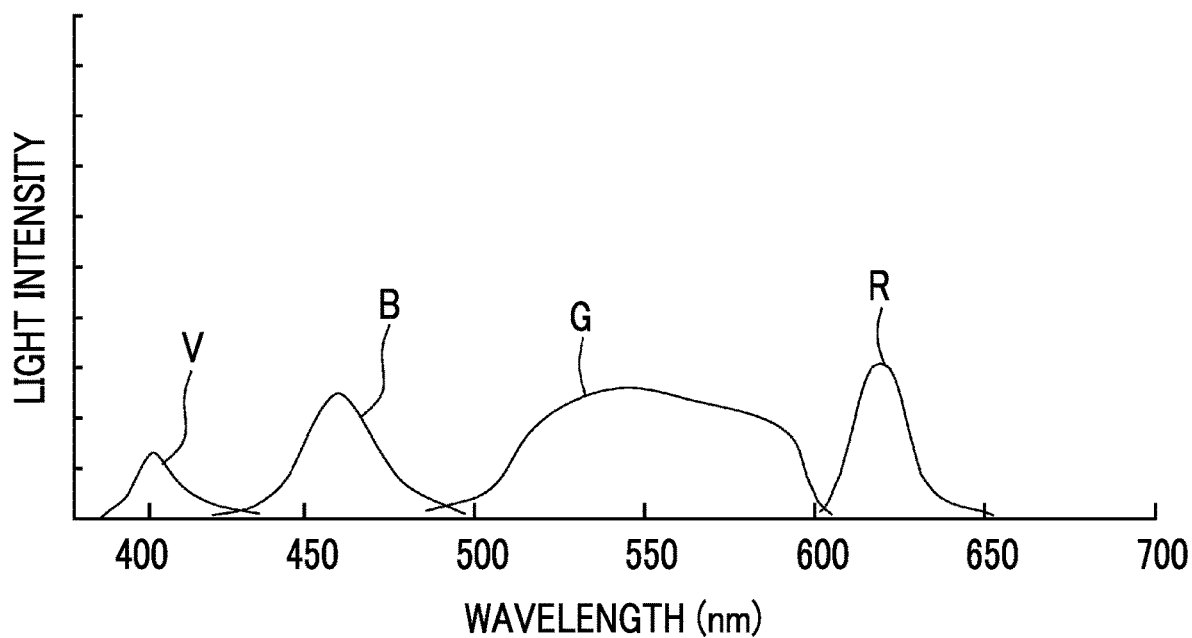
FIG. 3 is a graph showing the emission spectra of violet light V, blue light B, green light G, and red light R.

As shown in FIG. 3, the V-LED 20a generates violet light V of which the central wavelength is in the range of 405±10 nm and the wavelength range is in the range of 380 to 420 nm. The B-LED 20b generates blue light B of which the central wavelength is in the range of 460±10 nm and the wavelength range is in the range of 420 to 500 nm. The G-LED 20c generates green light G of which the wavelength range is in the range of 480 to 600 nm. The R-LED 20d generates red light R of which the central wavelength is in the range of 620 to 630 nm and the wavelength range is in the range of 600 to 650 nm.

The light source control unit 21 performs control to turn on the V-LED 20a, the B-LED 20b, the G-LED 20c, and the R-LED 20d in all observation modes. Further, the light source control unit 21 controls the respective LEDs 20a to 20d so that normal light of which the light emission ratios of violet light V, blue light B, green light G, and red light R are Vc:Bc:Gc:Rc is emitted in the normal observation mode.

Figure 4:
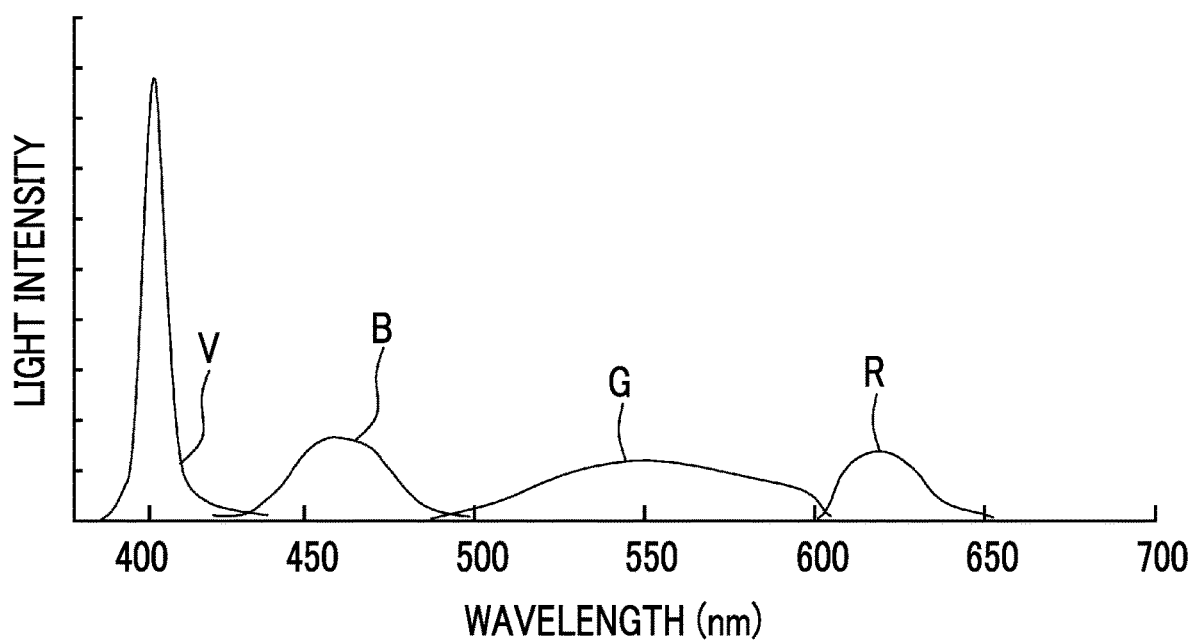
FIG. 4 is a graph showing the emission spectrum of first special light that includes violet light V, blue light B, green light G, and red light R.

Furthermore, the light source control unit 21 controls the respective LEDs 20a to 20d so that first special light of which the light emission ratios of violet light V, blue light B, green light G, and red light R are Vs1:Bs1:Gs1:Rs1 is emitted in the first special observation mode. To emphasize superficial blood vessels, it is preferable that the first special light has a peak in the range of 400 nm to 440 nm. For this purpose, the light emission ratios Vs1:Bs1:Gs1:Rs1 of the first special light are set so that the light intensity of violet light V is higher than the light intensity of each of blue light B, green light G, and red light R as shown in FIG. 4 (Vs1>Bs1, Gs1, and Rs1). Further, since the first special light includes a first red-light wavelength range like red light R, the first special light can accurately reproduce the color of a mucous membrane. Furthermore, since the first special light includes a first blue-light wavelength range and a first green-light wavelength range like violet light V, blue light B, and green light G, the first special light can also emphasize various structures, such as glandular structures and unevenness, in addition to the above-mentioned superficial blood vessels.

Further, the light source control unit 21 controls the respective LEDs 20a to 20d so that second special light of which the light emission ratios of violet light V, blue light B, green light G, and red light R are Vs2:Bs2:Gs2:Rs2 is emitted in the second special observation mode. To emphasize deep blood vessels, it is preferable that the intensity ratios of pieces of light having wavelengths of 540 nm, 600 nm, and 630 nm of the second special light are higher than those of the first special light.

Figure 5:
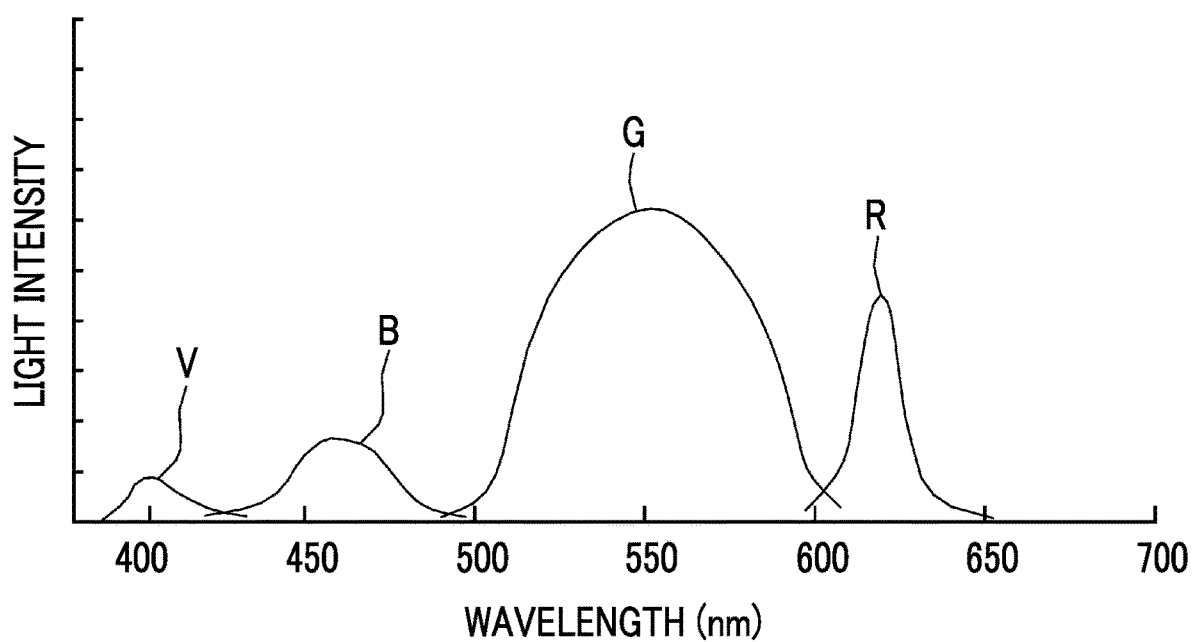
FIG. 5 is a graph showing the emission spectrum of second special light that includes violet light V, blue light B, green light G, and red light R.

For this purpose, the light emission ratios Vs2:Bs2:Gs2:Rs2 of the second special light are set so that the amounts of blue light B, green light G, and red light R of the second special light are larger than the amounts of blue light B, green light G, and red light R of the first special light as shown in FIG. 5. Further, the light emission ratios Vs2:Bs2:Gs2:Rs2 are set so that the light intensity of violet light V is lower than the light intensity of each of blue light B, green light G, and red light R (Vs2<Bs2, Gs2, and Rs2). Furthermore, since the second special light includes a second red-light wavelength range like red light R, the second special light can accurately reproduce the color of a mucous membrane. Moreover, since the second special light includes a second blue-light wavelength range and a second green-light wavelength range like violet light V, blue light B, and green light G, the second special light can also emphasize various structures, such as glandular structures and unevenness, in addition to the above-mentioned deep blood vessels.

In a case where a mode is to be switched, the light source control unit 21 provides a switching period of at least one or more frames and controls the respective LEDs 20a to 20d in this switching period so that switching-period-illumination light used to suppress the generation of an abnormal image to be generated at the time of the switching of a mode is emitted. An abnormal image is generated in a case where processing not corresponding to illumination light is performed as described later by the processor device 16 since time required for the switching of processing (gain processing, color adjustment processing, and the like) performed by the processor device 16 is longer than time required for the change of light emission ratios performed by the light source device 14. It is preferable that providing the switching period and emitting switching-period-illumination light in the switching period are performed at the time of at least one or more of the switching of a mode between the normal observation mode and the first special observation mode, the switching of a mode between the normal observation mode and the second special observation mode, and the switching of a mode between the first special observation mode and the second special observation mode.

For example, the light source control unit 21 performs first switching-period-light-emission control in the switching period to make light emission ratios be gradually close to the light emission ratios of second illumination light that have been subjected to switching from the light emission ratios of first illumination light that have not yet been subjected to switching. The first switching-period-light-emission control is to (seamlessly) emit switching-period-illumination light while gradually changing switching-period-light-emission ratios Vp(n):Bsp(n):Gp(n):Rp(n) (n is in the range of 1 to N. n and N are natural numbers). Accordingly, in the switching period, the generation of an abnormal image can be suppressed and an image that gives little sense of incongruity to a user can be acquired.

Figure 6:
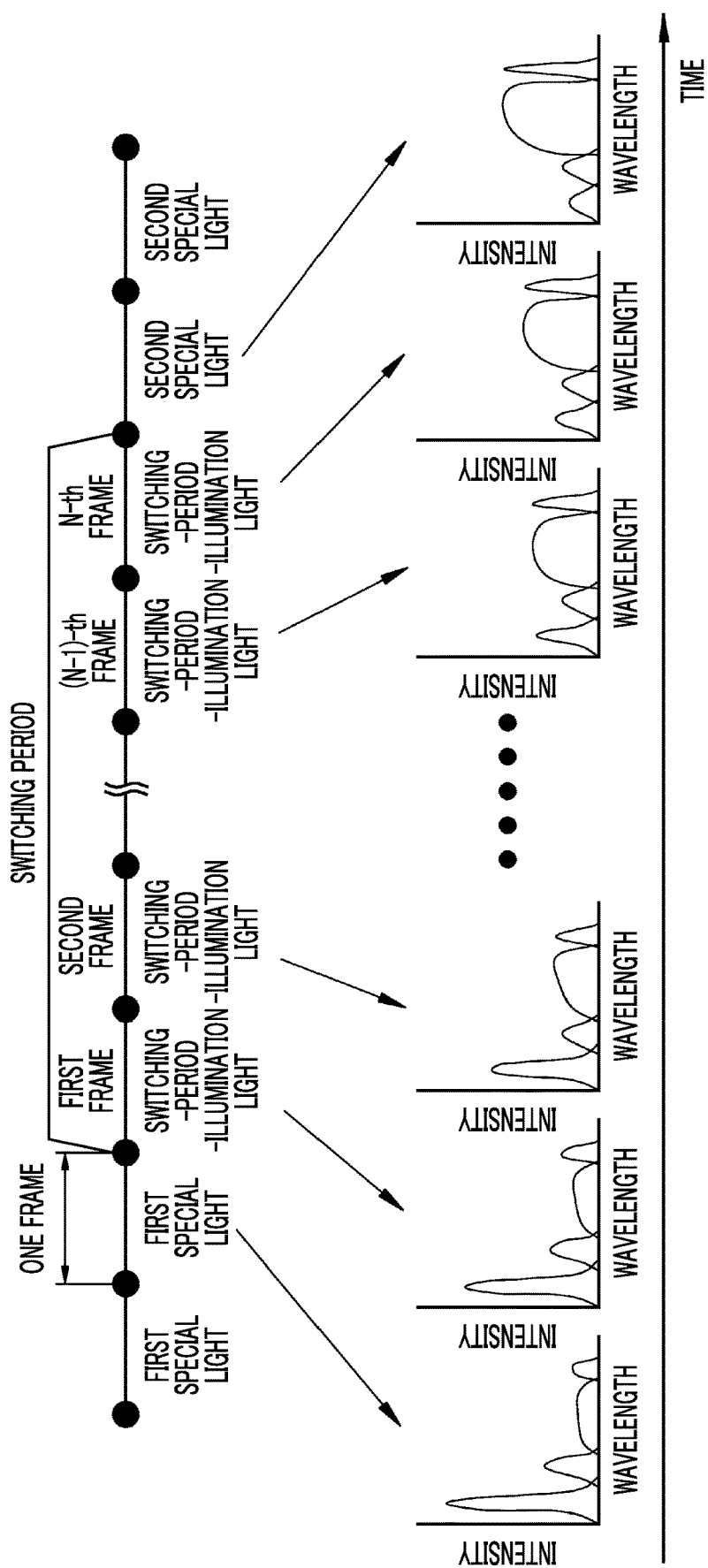
FIG. 6 is a diagram illustrating first switching-period-light-emission control.

For example, in a case where a mode is to be switched to the second special observation mode from the first special observation mode, the first switching-period-light-emission control is performed as described below. After the light emission period of the first special light (first illumination light) ends, a period is shifted to the switching period as shown in FIG. 6. Switching-period-illumination light of which the switching-period-light-emission ratios are Vp(1):Bp(1):Gp(1):Rp(1) is emitted in the first (initial) frame of the switching period (switching-period-first frame). The switching-period-light-emission ratios Vp(1):Bp(1):Gp(1):Rp(1) are light emission ratios where the light intensity of a short-wavelength component is set to be lower than that of the first special light and the light intensity of a long-wavelength component is set to be higher than that of the first special light. That is, at least "Vp(1)<Vs1" and "Rp(1)>Rs1" are satisfied.

Then, the switching-period-light-emission ratios are changed to Vp(2):Bp(2):Gp(2):Rp(2) and switching-period-illumination light is emitted in the next switching-period-second frame of the switching-period-first frame of the switching period. The switching-period-light-emission ratios Vp(2):Bp(2):Gp(2):Rp(2) are light emission ratios where the light intensity of a short-wavelength component is set to be lower than that of the switching-period-illumination light emitted in the switching-period-first frame and the light intensity of a long-wavelength component is set to be higher than that of the switching-period-illumination light emitted in the switching-period-first frame. That is, the switching-period-light-emission ratios Vp(2):Bp(2):Gp(2):Rp(2) satisfy at least "Vp(2)<Vp(1)" and "Rp(2)>Rp(1)".

Subsequently, switching-period-light-emission ratios Vp(n):Bp(n):Gp(n):Rp(n) are changed in the same way as described above so that the light intensity of the short-wavelength component of the switching-period-illumination light becomes lower and the light intensity of the long-wavelength component thereof becomes higher as it goes to a later frame in the switching period. That is, the switching-period-light-emission ratios Vp(n):Bp(n):Gp(n):Rp(n) are changed to satisfy at least "Vp(n+1)<Vp(n)" and "Rp(n+1)>Rp(n)".

Then, switching-period-illumination light of which the switching-period-light-emission ratios Vp(N):Bp(N):Gp(N):Rp(N) are close to the light emission ratios Vs2:Bs2:Gs2:Rs2 of the second special light (second illumination light) is emitted in the final frame of the switching period (switching-period-N-th frame). The light intensity of the short-wavelength component of the switching-period-illumination light emitted in the switching-period-N-th frame is slightly higher than that of the second special light and the light intensity of the long-wavelength component thereof is slightly lower than that of the second special light, but the wavelength spectrum of the switching-period-illumination light emitted in the switching-period-N-th frame is substantially close to that of the second special light. That is, at least "Vp(N)>Vs2" and "Rp(N)<Rs2" are satisfied.

Figure 7:
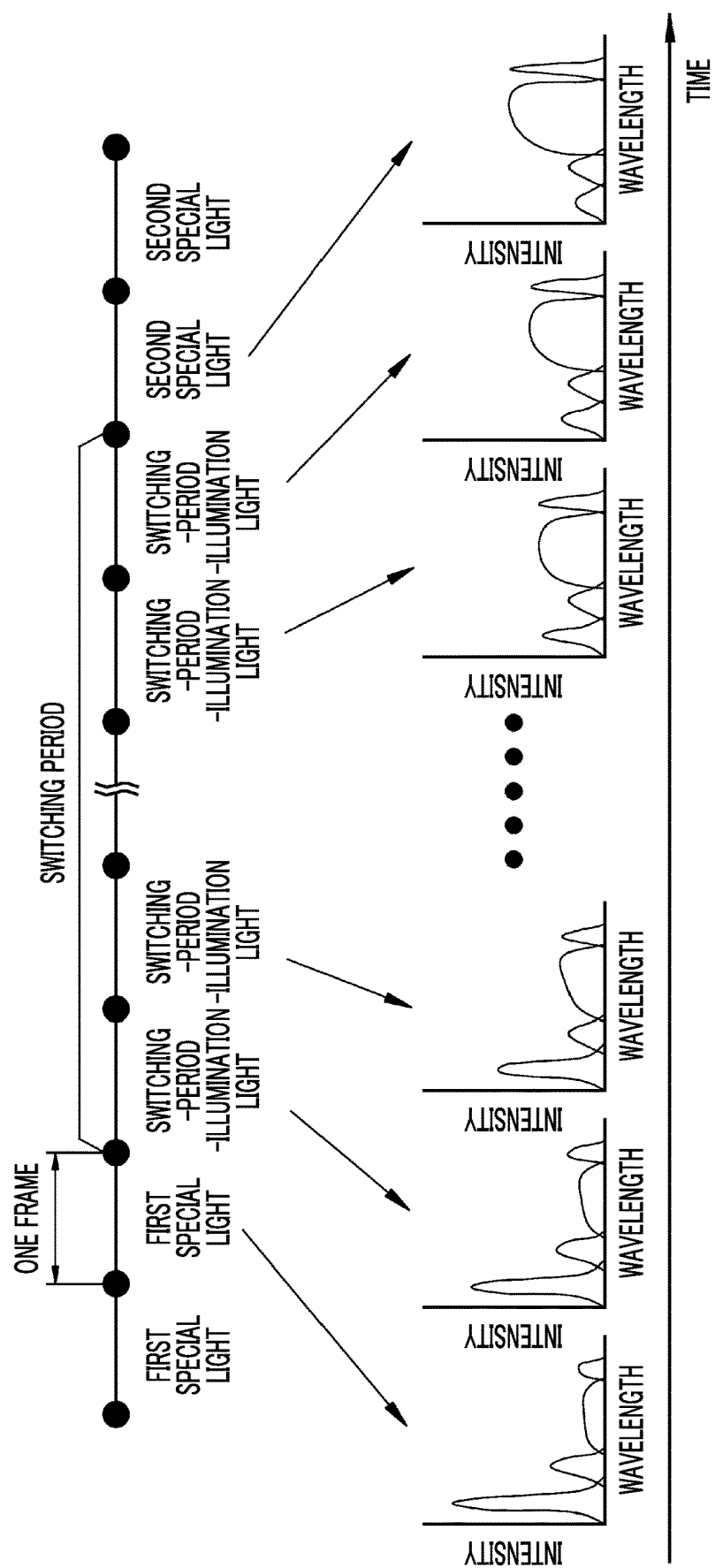
FIG. 7 is a diagram illustrating second switching-period-light-emission control.

Further, as shown in FIG. 7, the light source control unit 21 performs second switching-period-light-emission control in the switching period to prevent light emission ratios from being suddenly changed to the light emission ratios of the second illumination light that have been subjected to switching from the light emission ratios of the first illumination light that have not yet been subjected to switching. The second switching-period-light-emission control is to emit switching-period-illumination light with switching-period-light-emission ratios Vpa:Bp:Gpa:Rpa that are ratios between the light emission ratios of the first illumination light and the light emission ratios of the second illumination light. Accordingly, in the switching period, the generation of an abnormal image can be suppressed and an image that gives little sense of incongruity to a user can be acquired.

For example, in a case where a mode is to be switched to the second special observation mode from the first special observation mode, switching-period-light-emission ratios Vspa:Bspa:Gspa:Rspa are set to ratios between the light emission ratios Vs1:Bs1:Gs1:Rs1 of the first special light and the light emission ratios Vs2:Bs2:Gs2:Rs2 of the second special light. It is preferable that the switching-period-light-emission ratios Vspa:Bspa:Gspa:Rspa are average ratios of the light emission ratios of the first special light and the light emission ratios of the second special light. That is, it is preferable that "Vspa=(Vs1+Vs2)/2", "Bspa=(Bs1+Bs2)/2", "Gspa=(Gs1+Gs2)/2", and "Rspa=(Rs1+Rs2)/2" are satisfied.

One of the first switching-period-light-emission control and the second switching-period-light-emission control that is to be performed by the light source control unit 21 can be set by the console 19. Further, a switching period in a case where the first switching-period-light-emission control is to be performed and a switching period in a case where the second switching-period-light-emission control is to be performed can also be appropriately set by the console 19. Here, it is preferable that a switching period is set to be longer in the case of the first switching-period-light-emission control to obtain an image giving less sense of incongruity to a user. For example, it is preferable that a switching period in a case where the first switching-period-light-emission control is to be performed is set to be longer than a switching period in a case where the second switching-period-light-emission control is to be performed.

As shown in FIG. 2, the light guide 41 is built in the endoscope 12 and a universal cord (a cord connecting the endoscope 12 to the light source device 14 and the processor device 16), and transmits the pieces of light, which are combined by the optical path-combination unit 23, to the distal end part 12d of the endoscope 12. A multimode fiber can be used as the light guide 41. For example, a thin fiber cable of which a total diameter of a core diameter of 105 µm, a cladding diameter of 125 µm, and a protective layer forming a covering is in the range of ϕ0.3 to 0.5 mm can be used.

The distal end part 12d of the endoscope 12 is provided with an illumination optical system 30a and an image pickup optical system 30b. The illumination optical system 30a includes an illumination lens 45, and an object to be observed is irradiated with light transmitted from the light guide 41 through the illumination lens 45. The image pickup optical system 30b includes an objective lens 46 and an image pickup sensor 48. Light reflected from the object to be observed is incident on the image pickup sensor 48 through the objective lens 46. Accordingly, the reflected image of the object to be observed is formed on the image pickup sensor 48.

The image pickup sensor 48 is a color image pickup sensor, and picks up the reflected image of an object to be examined and outputs image signals. It is preferable that the image pickup sensor 48 is a charge coupled device (CCD) image pickup sensor, a complementary metal-oxide semiconductor (CMOS) image pickup sensor, or the like. The image pickup sensor 48 used in the invention is a color image pickup sensor that is used to obtain RGB image signals corresponding to three colors of R (red), G (green), and B (blue), that is, a so-called RGB image pickup sensor that comprises R-pixels provided with R-filters, G-pixels provided with G-filters, and B-pixels provided with B-filters.

The image pickup sensor 48 may be a so-called complementary color image pickup sensor, which comprises complementary color filters corresponding to C (cyan), M (magenta), Y (yellow), and G (green), instead of an RGB color image pickup sensor. In a case where a complementary color image pickup sensor is used, image signals corresponding to four colors of C, M, Y, and G are output. Accordingly, the image signals corresponding to four colors of C, M, Y, and G need to be converted into image signals corresponding to three colors of R, G, and B by complementary color-primary color conversion. Further, the image pickup sensor 48 may be a monochrome image pickup sensor that includes no color filter. In this case, since the light source control unit 21 causes blue light B, green light G, and red light R to be emitted in a time-sharing manner, demosaicing needs to be added to the processing of image pickup signals.

The image signals output from the image pickup sensor 48 are transmitted to a CDS/AGC circuit 50. The CDS/AGC circuit 50 performs correlated double sampling (CDS) or auto gain control (AGC) on the image signals that are analog signals. The image signals, which have been transmitted through the CDS/AGC circuit 50, are converted into digital image signals by an analog/digital converter (A/D converter) 52. The digital image signals, which have been subjected to A/D conversion, are input to the processor device 16.

The processor device 16 corresponds to a medical image processing device that processes medical images, such as images obtained by the endoscope 12. The processor device 16 comprises an image acquisition unit 53, a digital signal processor (DSP) 56, a noise removing unit 58, an image processing unit 60, a parameter switching unit 62, a video signal generation unit 66, and a central control unit 68. Digital color image signals output from the endoscope 12 are input to the image acquisition unit 53. The color image signals are RGB image signals formed of R-image signals that are output from the R-pixels of the image pickup sensor 48, G-image signals that are output from the G-pixels of the image pickup sensor 48, and B-image signals that are output from the B-pixels of the image pickup sensor 48.

The DSP 56 performs various kinds of signal processing, such as defect correction processing, offset processing, gain processing, color adjustment processing, gamma conversion processing, and demosaicing processing, on the received image signals. Signals of defective pixels of the image pickup sensor 48 are corrected in the defect correction processing. Dark current components are removed from the RGB image signals having been subjected to the defect correction processing in the offset processing, so that an accurate zero level is set.

The RGB image signals having been subjected to the offset processing are multiplied by a specific gain parameter in the gain processing, so that signal levels are adjusted. The specific gain parameter varies depending on each observation mode. For example, gain processing for normal light for multiplying image signals, which are obtained from illumination using normal light and image pickup, and a gain parameter for normal light as the specific gain parameter together is performed in the normal observation mode. Further, gain processing for first special light for multiplying RGB image signals (first image), which are obtained from illumination using first special light and image pickup, and a gain parameter for first special light as the specific gain parameter together is performed in the first special observation mode. Furthermore, gain processing for second special light for multiplying RGB image signals (second image), which are obtained from illumination using second special light and image pickup, and a gain parameter for second special light as the specific gain parameter together is performed in the second special observation mode.

After that, brightness or a saturation is adjusted by the gamma conversion processing. The demosaicing processing (also referred to as equalization processing or demosaicing) is performed on the RGB image signals having been subjected to linear matrix processing, so that signals of colors deficient in each pixel are generated by interpolation. All the pixels are made to have the signals of the respective colors of R, G, and B by this demosaicing processing.

The noise removing unit 58 performs noise removal processing (for example, a moving-average method, median filtering, or the like) on the RGB image signals, which have been subjected to gamma correction and the like by the DSP 56, to remove noise from the RGB image signals. The RGB image signals from which noise has been removed are transmitted to the image processing unit 60.

The image processing unit 60 performs various kinds of image processing on the RGB image signals. The various kinds of image processing include image processing that is performed under a condition varying depending on each observation mode in addition to image processing that is performed under the same condition irrespective of the observation mode. The image processing that is performed under a condition varying depending on each observation mode includes color adjustment processing for improving color reproducibility and structure emphasis processing for emphasizing various structures, such as blood vessels and unevenness. The color adjustment processing and the structure emphasis processing are processing that uses a two-dimensional look up table (LUT), a three-dimensional LUT, a matrix, or the like. In a case where the image processing unit 60 performs color emphasis processing and structure emphasis processing, a color-emphasis-processing parameter and a structure-emphasis-processing parameter set for each observation mode are used in the image processing unit 60. The switching of the color-emphasis-processing parameter or the structure-emphasis-processing parameter is performed by the parameter switching unit 62 according to the operation of the mode changeover SW 13a.

In a case where a mode is set to the normal observation mode by the mode changeover SW 13a, a color-emphasis-processing parameter and a structure-emphasis-processing parameter are switched to a color-emphasis-processing parameter for normal light and a structure-emphasis-processing parameter for normal light in the image processing unit 60 by the parameter switching unit 62. Then, the image processing unit 60 performs color emphasis processing for normal light on the RGB image signals by using the color-emphasis-processing parameter for normal light, and performs structure emphasis processing for normal light on the RGB image signals by using the structure-emphasis-processing parameter for normal light. After that, the RGB image signals having been subjected to other image processing corresponding to the normal observation mode are input to the video signal generation unit 66 as the normal image.

In a case where a mode is set to the first special observation mode by the mode changeover SW 13a, a color-emphasis-processing parameter and a structure-emphasis-processing parameter are switched to a color-emphasis-processing parameter for first special light and a structure-emphasis-processing parameter for first special light in the image processing unit 60 by the parameter switching unit 62. Then, the image processing unit 60 performs color emphasis processing for first special light on the RGB image signals by using the color-emphasis-processing parameter for first special light, and performs structure emphasis processing for first special light on the RGB image signals by using the structure-emphasis-processing parameter for first special light. After that, the RGB image signals having been subjected to other image processing corresponding to the first special observation mode are input to the video signal generation unit 66 as the first special image.

In a case where a mode is set to the second special observation mode by the mode changeover SW 13a, a color-emphasis-processing parameter and a structure-emphasis-processing parameter are switched to a color-emphasis-processing parameter for second special light and a structure-emphasis-processing parameter for second special light in the image processing unit 60 by the parameter switching unit 62. Then, the image processing unit 60 performs color emphasis processing for second special light on the RGB image signals by using the color-emphasis-processing parameter for second special light, and performs structure emphasis processing for second special light on the RGB image signals by using the structure-emphasis-processing parameter for second special light. After that, the RGB image signals having been subjected to other image processing corresponding to the second special observation mode are input to the video signal generation unit 66 as the second special image.

The video signal generation unit 66 converts the normal image, the first special image, or the second special image, which is input from the image processing unit 60, into video signals used to display the normal image, the first special image, or the second special image as an image that can be displayed by the monitor 18. The monitor 18 displays the normal image, the first special image, or the second special image on the basis of the video signals.

The central control unit 68 performs the control of each part of the processor device 16. Further, the central control unit 68 receives information output from the endoscope 12 or the light source device 14, and performs the control of each part of the processor device 16 and the control of the endoscope 12 or the light source device 14 on the basis of the received information.

Figure 8:
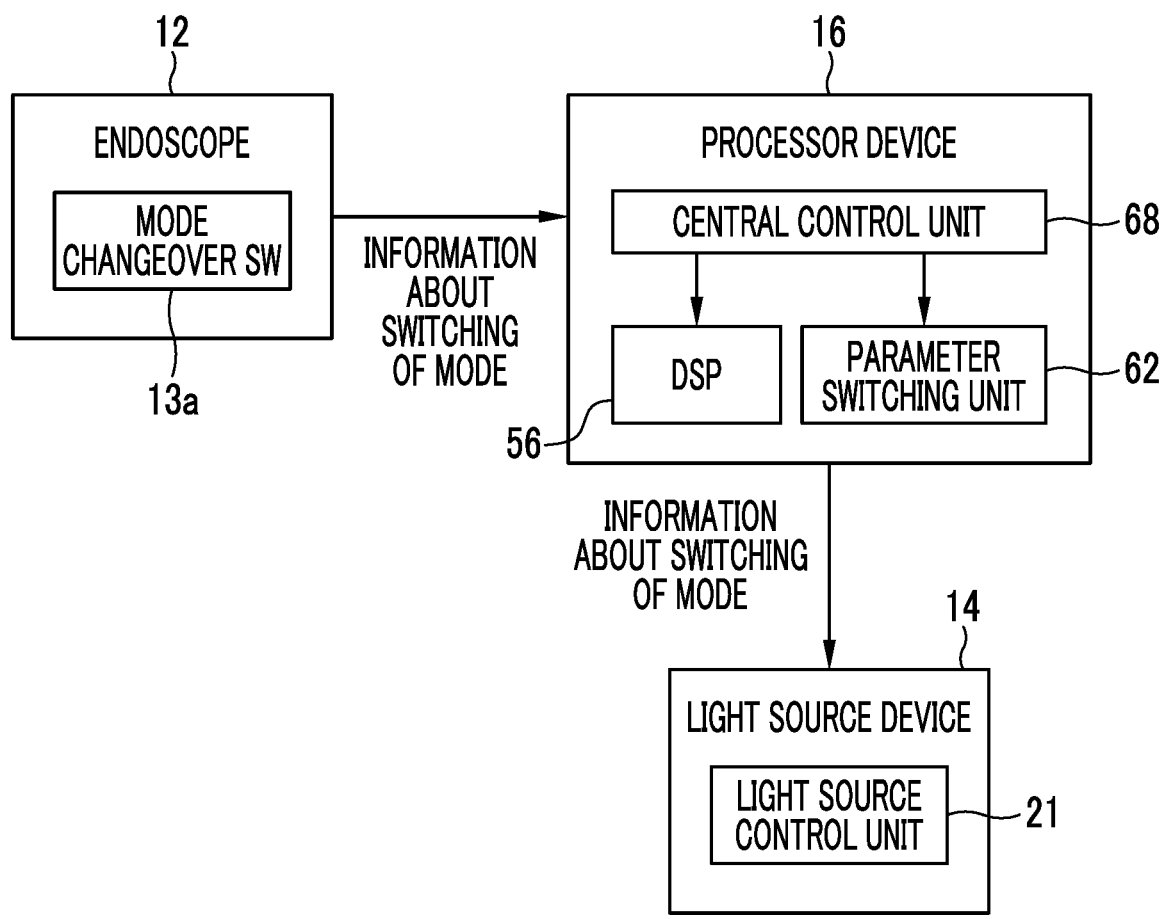
FIG. 8 is a block diagram showing the flow of information in a case where an operation for switching a mode is performed.

For example, as shown in FIG. 8, information about the switching of a mode is transmitted to the central control unit 68 in a case where the mode changeover SW 13a of the endoscope 12 is operated. In a case where the central control unit 68 receives the information about the switching of a mode, the central control unit 68 instructs the light source device 14 to emit switching-period-illumination light in the switching period. In a case where the light source device 14 receives an instruction to emit switching-period-illumination light, the light source control unit 21 emits switching-period-illumination light. The light source control unit 21 can perform light source control almost without requiring time from an instruction given from the central control unit 68. For example, the light emission ratios can be changed within one frame from the operation of the mode changeover SW 13a.

Further, in a case where the central control unit 68 receives the information about the switching of a mode, the central control unit 68 instructs the DSP 56 or the image processing unit 60, which are provided in the processor device 16, to change each processing by the switching of a mode. For example, in a case where a mode is switched to the second special observation mode from the first special observation mode, the DSP 56 switches gain processing to the gain processing for second special light from the gain processing for first special light by switching a gain parameter to the gain parameter for second special light from the gain parameter for first special light. Further, the parameter switching unit 62 switches color adjustment processing to color adjustment processing for second special light from color adjustment processing for first special light by switching a color-adjustment-processing parameter to a color-adjustment-processing parameter for second special light from a color-adjustment-processing parameter for first special light. Furthermore, the parameter switching unit 62 switches structure emphasis processing to the structure emphasis processing for second special light from the structure emphasis processing for first special light by switching a structure-emphasis-processing parameter to the structure-emphasis-processing parameter for second special light from the structure-emphasis-processing parameter for first special light.

The switching of the gain processing, the color adjustment processing, and the like having been described are often not immediately performed due to the status of processing in the processor device 16 and the like. For example, there is a case where two or more frames are required from the operation of the mode changeover SW 13a to the completed switching of the gain processing, the color adjustment processing, and the like.

Accordingly, it is preferable that a switching period is set to be longer than time required for the switching of processing to be used after the switching of a mode, such as gain processing or color adjustment processing. However, in a case where processing is switched to processing to be used after the switching of a mode even though a switching period does not end, it is preferable that the light emission ratios of switching-period-illumination light are switched so as to correspond to specific color balance according to this. It is preferable that the specific color balance is, for example, white balance.

Figure 9:
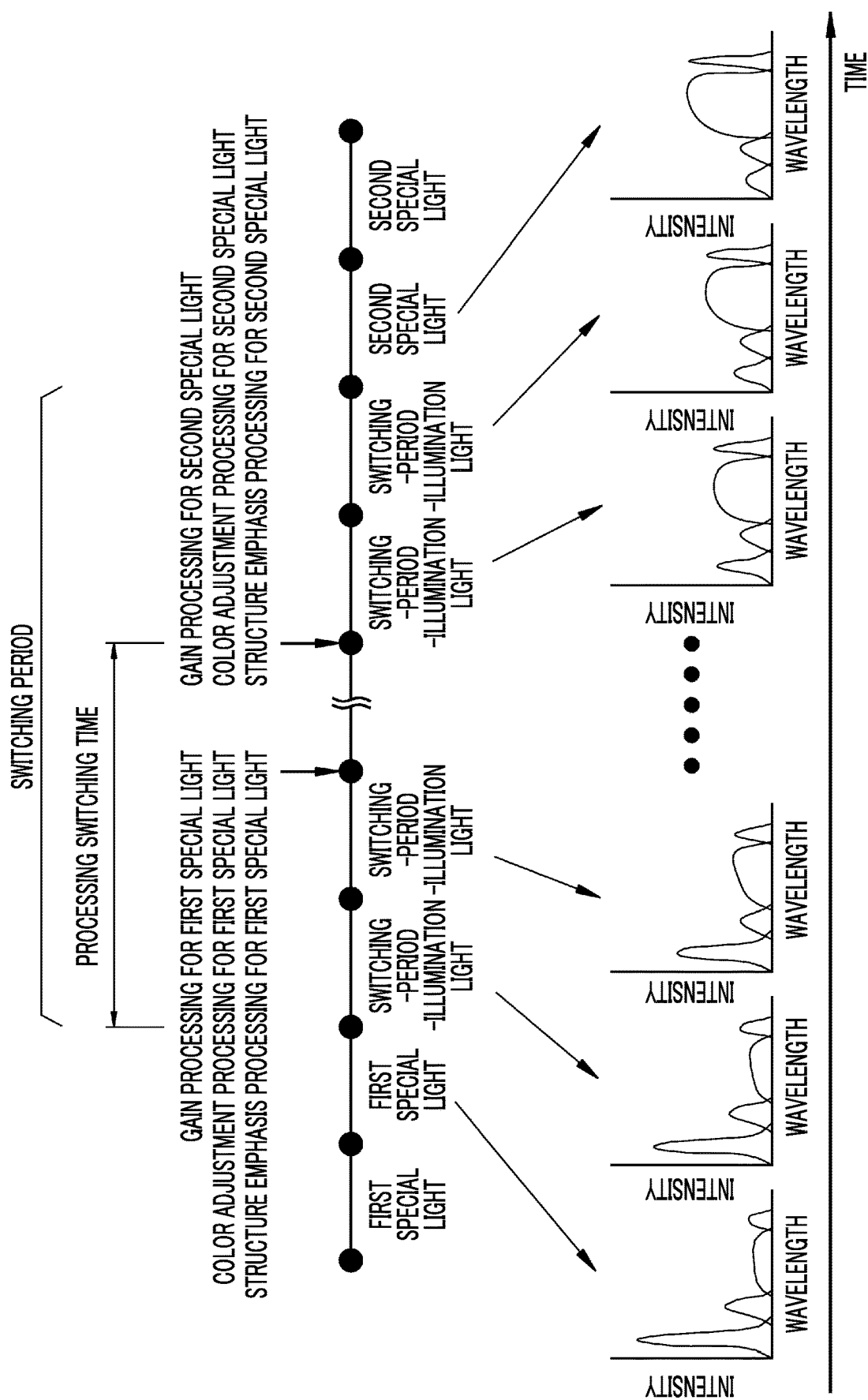
FIG. 9 is a diagram illustrating the switching of gain processing and color adjustment processing in a switching period.

For example, in a case where the first special observation mode is switched to the second special observation mode, gain processing is switched to the gain processing for second special light (processing for second illumination light) from the gain processing for first special light (processing for first illumination light) in a switching period as shown in FIG. 9. Further, color adjustment processing is switched to the color adjustment processing for second special light (processing for second illumination light) from the color adjustment processing for first special light (processing for first illumination light), and structure emphasis processing is switched to the structure emphasis processing for second special light (processing for second illumination light) from the structure emphasis processing for first special light (processing for first illumination light). Since time (the number of frames) required for the switching of gain processing or color adjustment processing is approximately known, the time required for the switching of gain processing or color adjustment processing is set in advance as processing switching time.

Accordingly, the light source control unit 21 changes the light emission ratios of switching-period-illumination light to light emission ratios corresponding to the specific color balance at a timing when the processing switching time has passed, that is, a timing when processing has been switched to the gain processing for second special light, the color adjustment processing for second special light, or the structure emphasis processing for second special light, in the switching period. The light emission ratios of switchingperiod-illumination light are maintained at the light emission ratios corresponding to the specific color balance between when the processing switching time has passed and when the switching period has ended. Since the light emission ratios of switching-period-illumination light are changed to light emission ratios corresponding to the specific color balance in this way to improve color reproducibility, a sense of incongruity to be given to a user can be reduced even before light emission ratios are switched to the light emission ratios of light having been subjected to switching.

Figure 10:
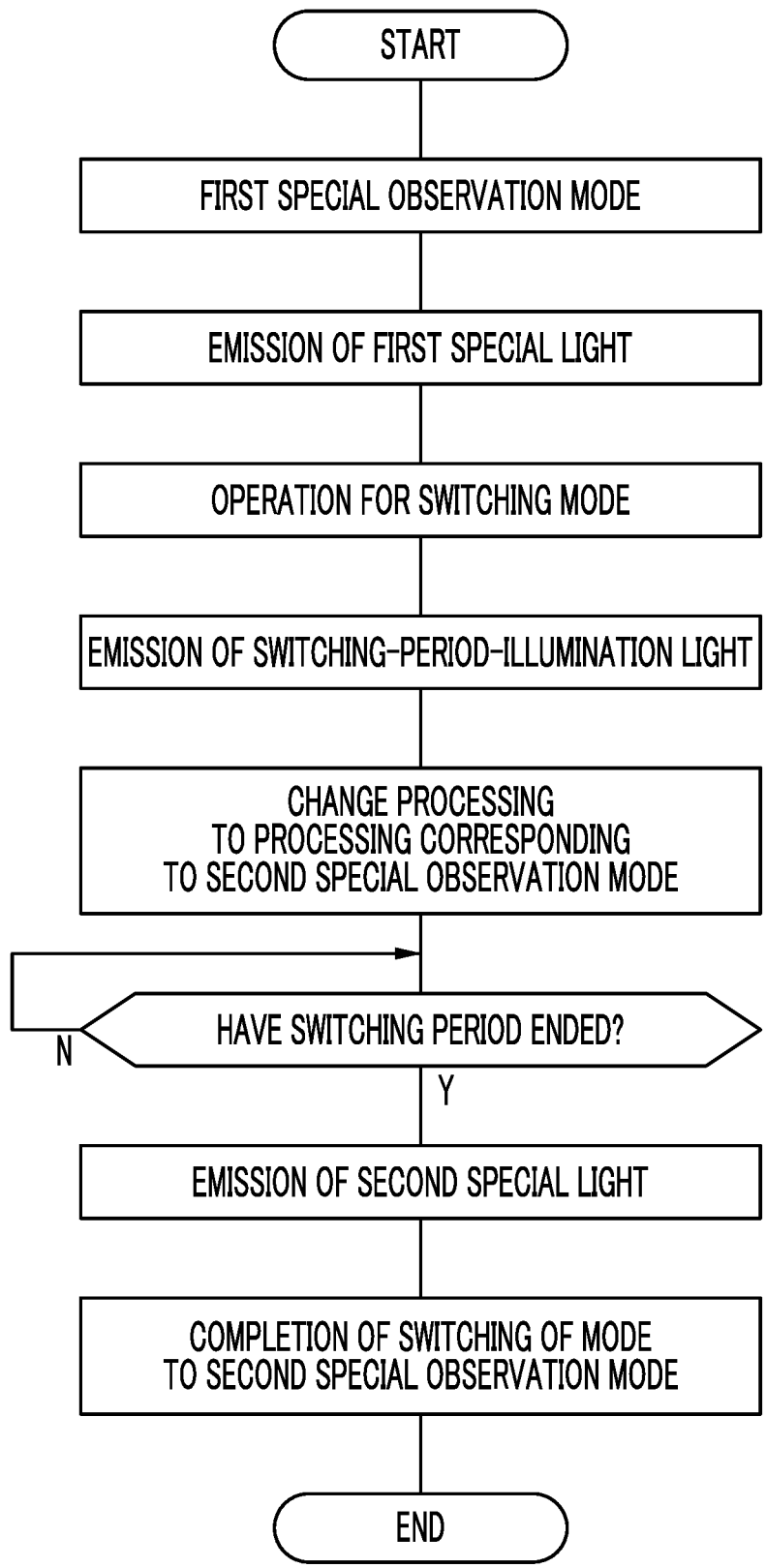
FIG. 10 is a flowchart showing the flow of light source control in a case where a mode is switched.

Next, light source control to be performed in a case where a mode is switched to the second special observation mode from the first special observation mode will be described with reference to a flowchart of FIG. 10. First special light of which the light emission ratios of violet light V, blue light B, green light G, and red light R are Vs1:Bs1:Gs1:Rs1 is emitted in the first special observation mode. Then, in a case where a mode is switched to the second special observation mode by the mode changeover SW 13a, information about the switching of a mode to the second special observation mode is transmitted to the central control unit 68 of the processor device 16.

In a case where the central control unit 68 receives the information about the switching of a mode to the second special observation mode, the central control unit 68 instructs the light source device 14 to emit switching-period-illumination light in the switching period. In the light source device 14, the light source control unit 21 performs control to emit switching-period-illumination light. Further, the central control unit 68 instructs the DSP 56 or the parameter switching unit 62, which is provided in the processor device 16, to change a parameter to a parameter corresponding to the second special observation mode.

Accordingly, the DSP 56 switches a gain parameter to the gain parameter for second special light from the gain parameter for first special light. Therefore, gain processing is switched to the gain processing for second special light from the gain processing for first special light. Further, the parameter switching unit 62 switches a color-adjustment-processing parameter to the color-adjustment-processing parameter for second special light from the color-adjustment-processing parameter for first special light. Accordingly, color adjustment processing is switched to the color adjustment processing for second special light from the color adjustment processing for first special light. Further, the parameter switching unit 62 switches a structure-emphasis-processing parameter to the structure-emphasis-processing parameter for second special light from the structure-emphasis-processing parameter for first special light. Accordingly, structure emphasis processing is switched to the structure emphasis processing for second special light from the color adjustment processing for first special light. Second special light of which the light emission ratios of violet light V, blue light B, green light G, and red light R are Vs2:Bs2:Gs2:Rs2 is emitted after the switching period ends. Accordingly, the switching of a mode to the second special observation mode is completed.

Second Embodiment

In a second embodiment, an object to be observed is illuminated using laser light sources and a fluorescent body instead of the four color LEDs 20a to 20d described in the first embodiment. Others are the same as those of the first embodiment.

Figure 11:
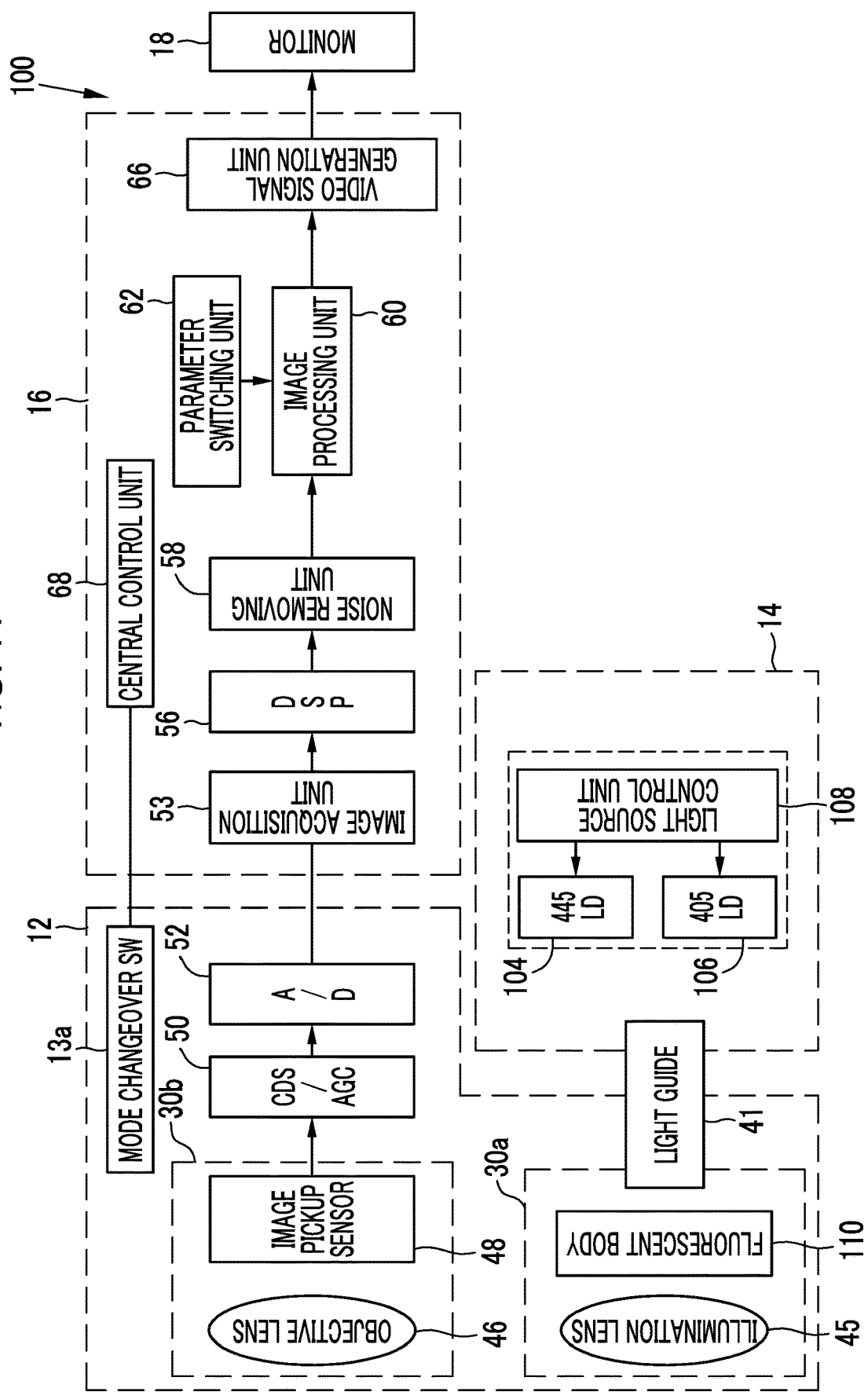
FIG. 11 is a block diagram showing the functions of an endoscope system according to a second embodiment.

As shown in FIG. 11, in an endoscope system 100 according to a second embodiment, a light source device 14 is provided with a blue laser light source (written in FIG. 11 as "445LD") 104 emitting blue laser light of which the central wavelength is in the range of 445±10 nm and a blue-violet laser light source (written in FIG. 11 as "405LD") 106 emitting blue-violet laser light of which the central wavelength is in the range of 405±10 nm, instead of the four color LEDs 20a to 20d. Since pieces of light emitted from semiconductor light-emitting elements of the respective light sources 104 and 106 are individually controlled by a light source control unit 108, a ratio of the amount of light emitted from the blue laser light source 104 to the amount of light emitted from the blue-violet laser light source 106 can be freely changed.

The light source control unit 108 drives the blue laser light source 104 in a normal observation mode. In a first special observation mode, the light source control unit 108 drives both the blue laser light source 104 and the blue-violet laser light source 106 and controls blue-violet laser light and blue laser light so that a light emission ratio Lv1 of blue-violet laser light is higher than a light emission ratio Lb1 of blue laser light. In a second special observation mode, the light source control unit 108 drives both the blue laser light source 104 and the blue-violet laser light source 106 and controls blue-violet laser light and blue laser light so that a light emission ratio Lb2 of blue laser light is higher than a light emission ratio Lv2 of blue-violet laser light.

It is preferable that the half-width of blue laser light or blue-violet laser light is set to about ±10 nm. Further, broad area-type InGaN-based laser diodes can be used as the blue laser light source 104 and the blue-violet laser light source 106, and InGaNAs-based laser diodes or GaNAs-based laser diodes can also be used. Furthermore, a light emitter, such as a light emitting diode, may be used as the light source.

The illumination optical system 30a is provided with a fluorescent body 110 on which blue laser light or blue-violet laser light transmitted from the light guide 41 is to be incident in addition to the illumination lens 45. In a case where the fluorescent body 110 is irradiated with blue laser light, fluorescence is emitted from the fluorescent body 110. Further, a part of blue laser light passes through the fluorescent body 110 as it is. Blue-violet laser light passes through the fluorescent body 110 without exciting the fluorescent body 110. The inside of a specimen is irradiated with light, which is emitted from the fluorescent body 110, through the illumination lens 45.

Figure 12:
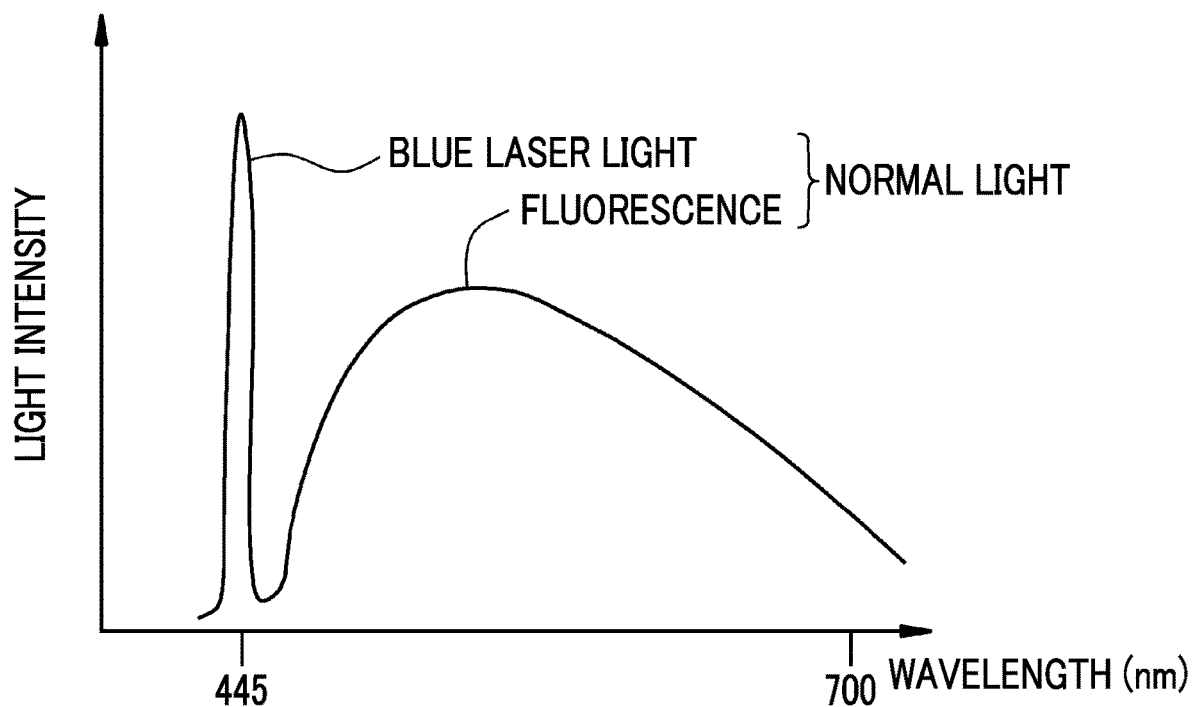
FIG. 12 is a graph showing the emission spectrum of normal light.
Figure 13:
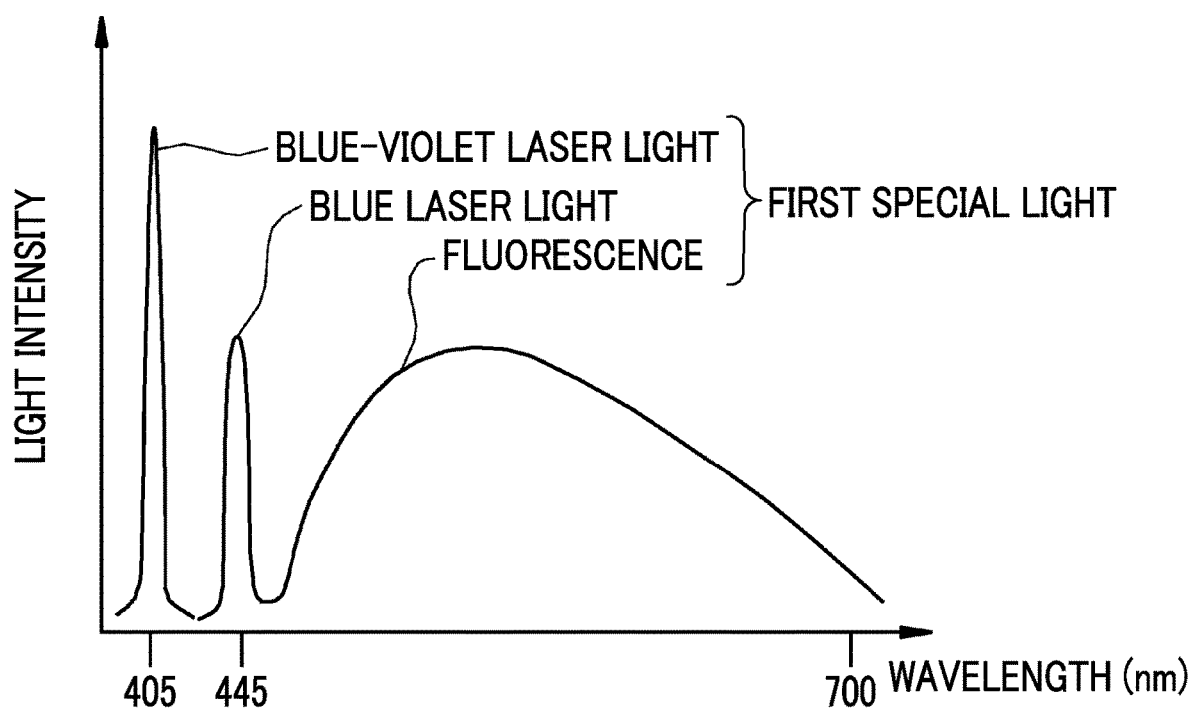
FIG. 13 is a graph showing the emission spectrum of first special light.

Here, since blue laser light is mainly incident on the fluorescent body 110 in the normal observation mode, an object to be observed is irradiated with normal light shown in FIG. 12 in which blue laser light and fluorescence excited and emitted from the fluorescent body 110 due to blue laser light are multiplexed. Since both blue-violet laser light and blue laser light are incident on the fluorescent body 110 in the first special observation mode, the inside of a specimen is irradiated with first special light shown in FIG. 13 in which blue-violet laser light, blue laser light, and fluorescence excited and emitted from the fluorescent body 110 due to blue laser light are multiplexed. In the first special light, the light intensity of blue-violet laser light is higher than the light intensity of blue laser light.

Figure 14:
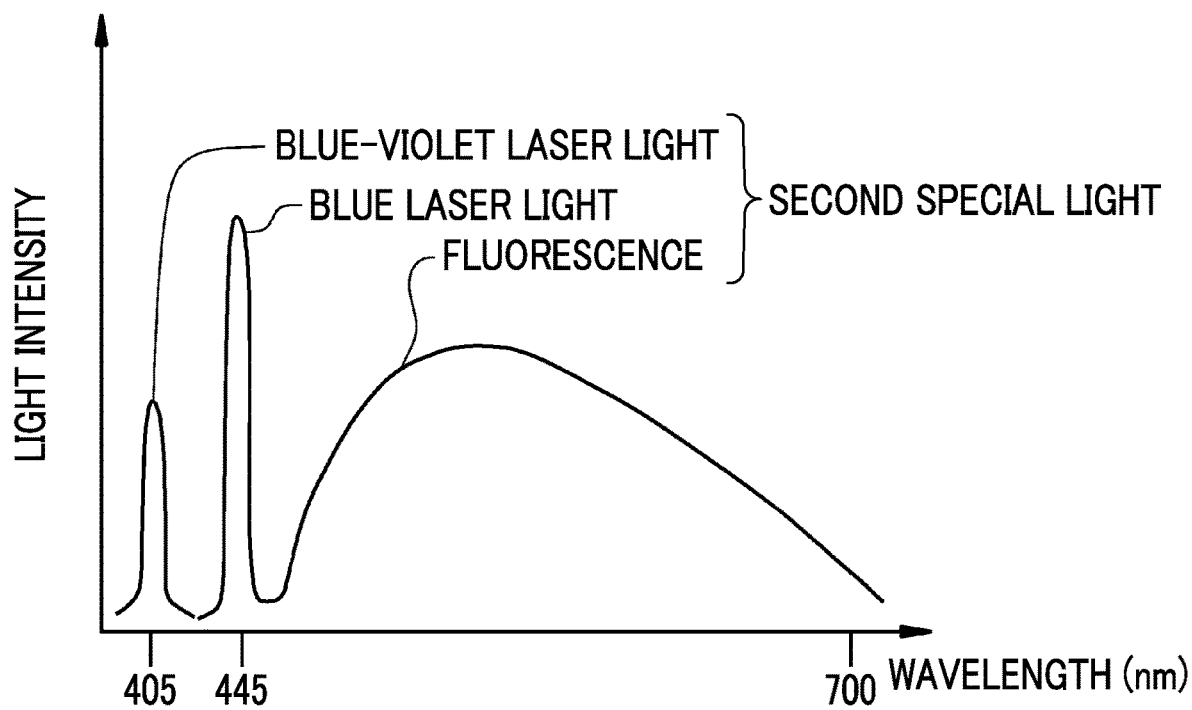
FIG. 14 is a graph showing the emission spectrum of second special light.

Since both blue-violet laser light and blue laser light are incident on the fluorescent body 110 even in the second special observation mode, the inside of a specimen is irradiated with second special light shown in FIG. 14 in which blue-violet laser light, blue laser light, and fluorescence excited and emitted from the fluorescent body 110 due to blue laser light are multiplexed. In the second special light, the light intensity of blue laser light is higher than the light intensity of blue-violet laser light.

Figure 15:
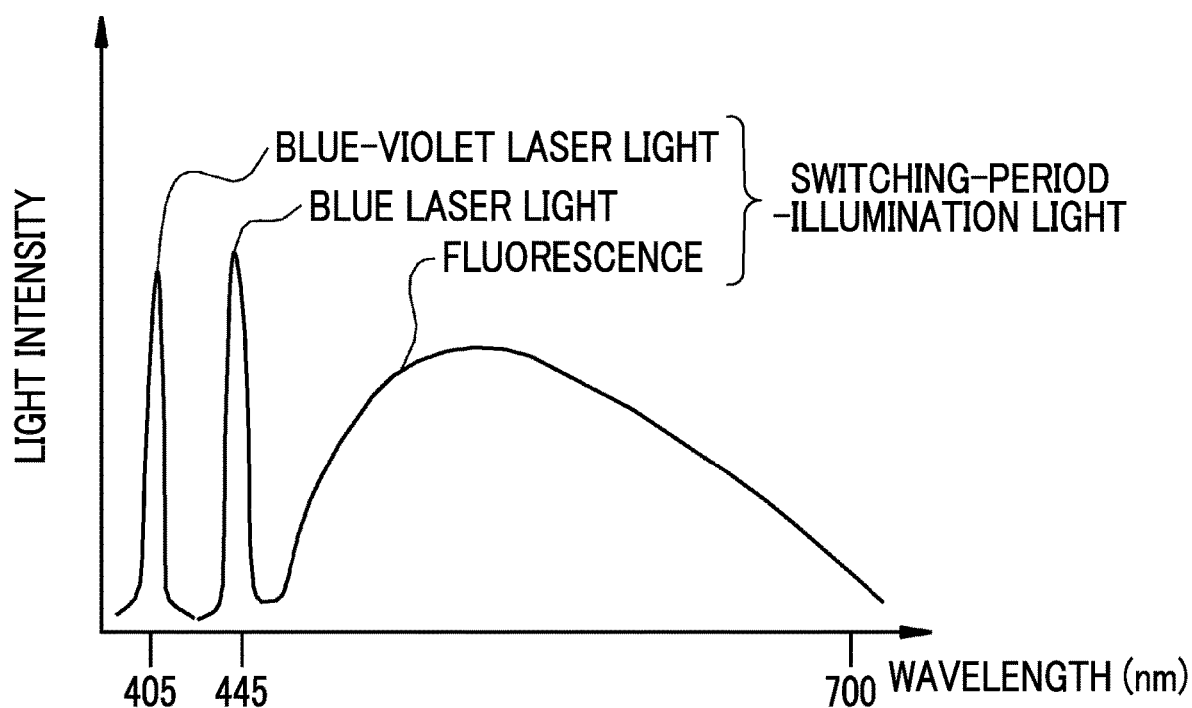
FIG. 15 is a graph showing the emission spectrum of switching-period-illumination light.

Even in the second embodiment, a switching period is provided and switching-period-illumination light is emitted in the switching period at the time of the switching of a mode. For example, in a case where a mode is to be switched to the second special observation mode from the first special observation mode, it is preferable to emit switching-period-illumination light of which a light emission ratio Lvp of blue-violet laser light is between the light emission ratio Lv1 of blue-violet laser light of the first special light and the light emission ratio Lv2 of blue-violet laser light of the second special light and a light emission ratio Lbp of blue laser light is between the light emission ratio Lb1 of blue laser light of the first special light and the light emission ratio Lb2 of blue laser light of the second special light as shown in FIG. 15.

It is preferable that a fluorescent body including plural kinds of fluorescent bodies absorbing a part of blue laser light and exciting and emitting green to yellow light (for example, YAG-based fluorescent bodies or fluorescent bodies, such as BAM ($BaMgAl_{10}O_{17}$)) is used as the fluorescent body 110. In a case where the semiconductor light-emitting elements are used as the excitation light source of the fluorescent body 110 as in this example of configuration, high-intensity white light is obtained with high luminous efficiency. Accordingly, not only the intensity of white light can be easily adjusted but also a change in the color temperature and chromaticity of white light can be suppressed to be small.

The hardware structures of the processing units, which are included in the processor device 16 in the embodiments, such as the image acquisition unit 53, the DSP 56, the noise removing unit 58, the image processing unit 60, the parameter switching unit 62, and the central control unit 68, are various processors to be described below. The various processors include: a central processing unit (CPU) that is a general-purpose processor functioning as various processing units by executing software (program); a programmable logic device (PLD) that is a processor of which circuit configuration can be changed after manufacture, such as a field programmable gate array (FPGA); a dedicated electrical circuit that is a processor having circuit configuration designed exclusively to perform various kinds of processing; and the like.

One processing unit may be formed of one of these various processors, or may be formed of a combination of two or more same kind or different kinds of processors (for example, a plurality of FPGAs or a combination of a CPU and an FPGA). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined.

EXPLANATION OF REFERENCES

10: endoscope system
12: endoscope
12a: insertion part
12b: operation part
12c: bendable part
12d: distal end part
12e: angle knob
14: light source device
16: processor device
18: monitor
19: console
20: light source unit
20a: V-LED
20b: B-LED
20c: G-LED
20d: R-LED
21: light source control unit
23: optical path-combination unit
30a: illumination optical system
30b: image pickup optical system
41: light guide
45: illumination lens
46: objective lens
48: image pickup sensor
50: CDS/AGC circuit
52: A/D converter
53: image acquisition unit
56: DSP
58: noise removing unit
60: image processing unit
62: parameter switching unit
63: first special image processing unit
64: second special image processing unit
66: video signal generation unit
68: central control unit
100: endoscope system
104: blue laser light source
106: blue-violet laser light source
108: light source control unit
110: fluorescent body

What is claimed is:

1. A light source device comprising:
a light source that emits light in a plurality of wavelength ranges and is capable of changing a light emission ratio of light in each wavelength range; and
a light source controller that performs control to emit switching-period-illumination light having a switching-period-light-emission ratio different from a first light emission ratio and a second light emission ratio in a switching period of at least one or more frames in a case where the light source controller performs switching of first illumination light having the first light emission ratio and second illumination light having the second light emission ratio different from the first light emission ratio, wherein
the light source controller performs first switching-period-light-emission control, which emits the switching-period-illumination light while changing the switching-period-light-emission ratio, in the switching period, and
each of the first illumination light, the second illumination light, and the switching-period-illumination light includes light in at least one wavelength range among the plurality of wavelength ranges.

2. The light source device according to claim 1, wherein the light source controller performs control in the first switching-period-light-emission control to make the switching-period-light-emission ratio become closer to a light emission ratio of illumination light to be emitted after the switching as it goes to a later frame in the switching period.

3. The light source device according to claim 1, wherein the light source controller performs second switching-period-light-emission control, which emits the switching-period-illumination light of which the switching-period-light-emission ratio is between the first light emission ratio and the second light emission ratio, in the switching period.

4. The light source device according to claim 1, wherein in a case where the light source controller performs second switching-period-light-emission control, which emits the switching-period-illumination light of which the switching-period-light-emission ratio is between the first light emission ratio and the second light emission ratio, in the switching period, the switching period of the first switching-period-light-emission control is set to be longer than the switching period in a case where the second switching-period-light-emission control is performed.

5. The light source device according to claim 1, wherein the switching-period-illumination light is emitted seamlessly while the switching-period-light-emission ratio is gradually changed.

6. An endoscope system comprising:
a light source device including
    a light source that emits light in a plurality of wavelength ranges and is capable of changing a light emission ratio of light in each wavelength range, and
    a light source controller that performs control to emit switching-period-illumination light having a switching-period-light-emission ratio different from a first light emission ratio and a second light emission ratio in a switching period of at least one or more frames in a case where the light source controller performs switching of first illumination light having the first light emission ratio and second illumination light having the second light emission ratio different from the first light emission ratio; and
a processor device that performs processing for first illumination light on a first image obtained from image pickup of an object to be observed illuminated with the first illumination light and performs processing for second illumination light on a second image obtained from image pickup of an object to be observed illuminated with the second illumination light, wherein
the light source controller performs control to make the switching-period-light-emission ratio correspond to specific color balance at a timing when processing has been switched to the processing for second illumination light from the processing for first illumination light,
the light source controller performs first switching-period-light-emission control, which emits the switching-period-illumination light while changing the switching-period-light-emission ratio, in the switching period, and
each of the first illumination light, the second illumination light, and the switching-period-illumination light includes light in at least one wavelength range among the plurality of wavelength ranges.

7. The endoscope system according to claim 6, wherein the processing for first illumination light is gain processing for first illumination light or color adjustment processing for first illumination light, and the processing for second illumination light is gain processing for second illumination light or color adjustment processing for second illumination light.

8. The endoscope system according to claim 6, wherein the switching-period-illumination light is emitted seamlessly while the switching-period-light-emission ratio is gradually changed.

9. A method of operating a light source device including a light source that emits light in a plurality of wavelength ranges and is capable of changing a light emission ratio of light in each wavelength range, the method comprising:
    an illumination light switching step in which a light source controller performs control to emit switching-period-illumination light having a switching-period-light-emission ratio different from a first light emission ratio and a second light emission ratio in a switching period of at least one or more frames in a case where switching of first illumination light having the first light emission ratio and second illumination light having the second light emission ratio different from the first light emission ratio is performed, wherein
    in the illumination light switching step, the light source controller performs first switching-period-light-emission control, which emits the switching-period-illumination light while changing the switching-period-light-emission ratio, in the switching period, and
    each of the first illumination light, the second illumination light, and the switching-period-illumination light includes light in at least one wavelength range among the plurality of wavelength ranges.

10. The method of operating a light source device according to claim 9, wherein
    in the illumination light switching step, the light source controller performs second switching-period-light-emission control, which emits the switching-period-illumination light of which the switching-period-light-emission ratio is between the first light emission ratio and the second light emission ratio, in the switching period.

11. The method of operating a light source device according to claim 9, wherein
    the switching-period-illumination light is emitted seamlessly while the switching-period-light-emission ratio is gradually changed.

* * * * *